United States Patent [19]

Jones

[11] Patent Number: 5,422,076
[45] Date of Patent: Jun. 6, 1995

[54] COMBINED URINE SPECIMEN BOTTLE AND CAP

[76] Inventor: R. Shane Jones, 1150 Sigman Rd., NE., Conyers, Ga. 30207

[21] Appl. No.: 145,882

[22] Filed: Oct. 29, 1993

Related U.S. Application Data

[63] Continuation-in-part of Ser. No. 666,686, Mar. 11, 1991, Pat. No. Des. 341,421.

[51] Int. Cl.$^6$ .................................................. B01L 3/00
[52] U.S. Cl. ................................. 422/102; 128/761; 604/317; 73/427; 206/569; 220/212.5; 220/307; 220/771
[58] Field of Search ............... 422/102, 104; 206/569, 206/438; 220/675, 307, 212.5, 769, 771; 73/426, 427; 128/760, 761; 604/317

[56] References Cited

U.S. PATENT DOCUMENTS

| | | | |
|---|---|---|---|
| Re. 33,686 | 9/1991 | Parrish | 128/771 |
| D. 297,462 | 8/1988 | Meunchen | D24/122 |
| D. 328,492 | 8/1992 | Mathis | D24/121 |
| 2,781,069 | 2/1957 | Byrd | 73/426 |
| 3,195,782 | 7/1965 | Eckley | 73/427 |
| 3,625,654 | 12/1971 | Van Dwyne | 422/102 |
| 3,699,815 | 10/1972 | Holbrook | 73/427 |
| 3,711,871 | 1/1973 | Sherin | 4/144.1 |
| 3,777,739 | 12/1973 | Raitto | 128/760 |
| 4,211,749 | 7/1980 | Kantner | 422/102 |
| 4,331,162 | 5/1982 | Kuntz et al. | 128/761 |
| 4,768,668 | 9/1988 | Van Den Brink | 220/307 |
| 5,129,892 | 7/1992 | McCarthy | 604/329 |
| 5,147,342 | 9/1992 | Kane et al. | 604/356 |
| 5,161,711 | 11/1992 | Picozza et al. | 220/307 |
| 5,203,836 | 4/1993 | Brazis et al. | 220/771 |
| 5,243,712 | 9/1993 | Cross | 4/144.2 |

Primary Examiner—James C. Housel
Assistant Examiner—Rachel Heather Freed
Attorney, Agent, or Firm—Kilpatrick & Cody

[57] ABSTRACT

An apparatus for sanitarily and easily collecting urine or other liquid specimens for testing, including a collection vessel having a handle portion and a cover. The relatively long, narrow dimensions of the collection vessel assure maneuverability. The handle also assists maneuverability, as well as facilitating sanitary collection of the specimen. The easy-to-use cover further ensures that the specimen remains free from contamination after collection, yet the user of the apparatus can readily and sanitarily seal the vessel.

9 Claims, 1 Drawing Sheet

COMBINED URINE SPECIMEN BOTTLE AND CAP

This application is a continuation-in-part of copending U.S. patent application Des. No. 07/666,686 (now U.S. Des. No. 341,421) filed Mar. 11, 1991 and having the same title.

BACKGROUND OF THE INVENTION

This invention relates to the collection of urine specimens for analysis and testing using an apparatus that includes a collection component and a cover component such that handling, labeling and sanitation is markedly more efficient and less expensive.

Analysis of urine specimens has long been, and remains, a crucial medical diagnostic tool. More recently such specimens have been collected for the purpose of identifying use of illegal drugs. Various devices to collect sanitarily such specimens have been devised. However, as disclosed in U.S. Pat. No. 3,777,739 issued to Raitto, women have long experienced difficulty using the normally narrow necked collection devices available.

Some attempts have been made at solving this need for better access and maneuverability without sacrificing sanitation or the purity of the specimen. For instance, U.S. Pat. No. 3,625,654 issued to Van Duyne describes a urine collection device specially designed to accommodate the physiological structure of the human body by means of an angled top. This collection device has a wide outer rim attached to a circular collection container. The opening of the container is cut at a 30° angle below horizonal (see column 2, lines 26–29). The wide, angled opening assures sanitary collection, especially when the device is releasably secured to a toilet bowl by its handle.

The prior art also discloses methods of preventing contamination of the urine specimen and vessel. For example, U.S. Pat. No. 4,331,162 issued to Kuntz, et al., discloses a device to collect the contaminant-free midstream portion of a female's urine specimen. More generally, U.S. Pat. No. 3,777,739 issued to Raitto describes (at column 1, lines 33–41) a container member, an intermediate member and a cap member enclosed in a protective covering. The Raitto device is provided as a unitary package with the cap member attached to the intermediate member, which in turn is attached to the collection member. Before giving a specimen, the user removes the cap member and maneuvers the collection part into position via the handle on the intermediate member and then fills the collection member. After filling, the user unscrews and discards the intermediate member, removes the cap member from the protective covering and carefully threads the cap member onto the filled container.

Other prior art also discloses circular containers with either threaded, e.g. U.S. Pat. No. 3,711,871 to Sherin, et al., or snap-on lids, e.g. U.S. Des. No. 328,492 issued to Mathis.

SUMMARY OF THE INVENTION

In the field of urine collection devices, simplicity for the user, sanitation and maneuverability, for women especially, are key design characteristics. While the prior art discloses many attempts to achieve separately any one such characteristic, the present invention incorporates all three to provide a simpler, more maneuverable and more sanitary device for the collection of urine.

The present invention is a vessel proportionally longer than it is wide. This relatively long, narrow structure allows for easier maneuvering and placement of the collection vessel for women, who generally must be sitting while using the vessel. Because the width of the collection vessel is proportionally less than the length, the sitting user has more ability to manipulate the vessel between the user's legs. Furthermore, the long handle, which may be reinforced for extra rigidity, is located above the plane of the opening to the vessel, thus allowing for even better maneuverability of the vessel. Such maneuverability allows the device to be readily used by even children or older adults, especially for female children or elderly females. Finally, the shield portion connecting the horizontal top of the vessel with the handle protects the user's hands from any splash caused by the forceful stream of exiting urine. This is particularly important for female users since in their normal sitting posture they are generally unable to lower the vessel sufficiently to mitigate the force of the exiting urine.

An additional feature of the present invention includes a snap-locking cover that can be placed on the vessel to seal the contents until transfer or analysis. Sealing the vessel with the cover requires only that the user press the cover into place, as the cover is normally dimensioned to slip into the vessel and thereby provide a waterproof seal by means of an annular ridge in the cover that is received in a mating recess in the vessel. This cover is much simpler to manufacture and use than the threaded and snap-on caps disclosed in the prior art, facilitating use of the present invention by children or elderly adults. For administrative convenience, the cover also contains an area upon which a label can be placed either with adhesive or through a sufficiently tight fit to keep the label frictionally engaged. Such a label is particularly useful where a large number of specimens are being collected in a relatively short time frame. Finally, a handle may be attached to the cover to facilitate its removal by the person analyzing or transferring the contents of the collection vessel; thus the chance of spilling or contaminating the urine specimen is further decreased.

An additional feature of the present invention is that its simplicity of design allows for lower manufacturing and sterilization costs. Manufacture of this invention can be accomplished through a vacuum thermo-forming or injection moulding process. Thus, the apparatus will be cost effective even though it will normally be disposed of after one use.

It is therefore an object of the present invention to provide an economical, simple-to-use sanitary collection vessel particularly suited for collection of female urine specimens but readily adaptable for usage by males.

It is another object of the present invention to provide an easily sealable collection vessel to prevent contamination or spilling of the specimen.

It is yet another object of the present invention to provide a collection device that avoids splashing or spilling of urine upon the hands of the person collecting the sample.

It is a further object of the present invention to provide a collection vessel that can be reliably stacked and stored both before and after filling.

It is an additional object of the present invention to provide a collection vessel which can be marked with graduations to indicate the amount of its contents in various units of measurement.

Other objects, features and advantages of the present invention will become apparent with reference to the remainder of the text and the drawings of this application.

DETAILED DESCRIPTION

Figure 1:
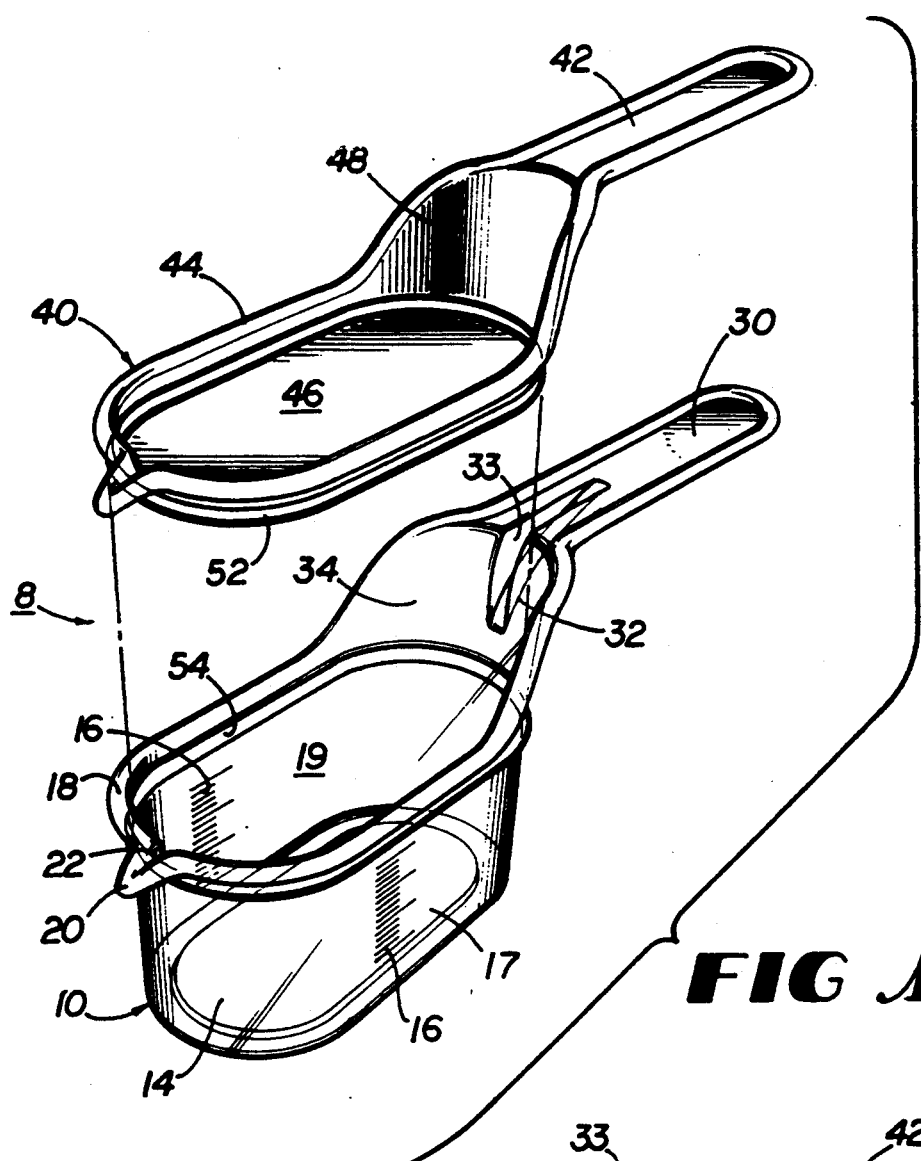
FIG. 1 is a perspective view of the collection vessel and cover of the present invention.
Figure 2:
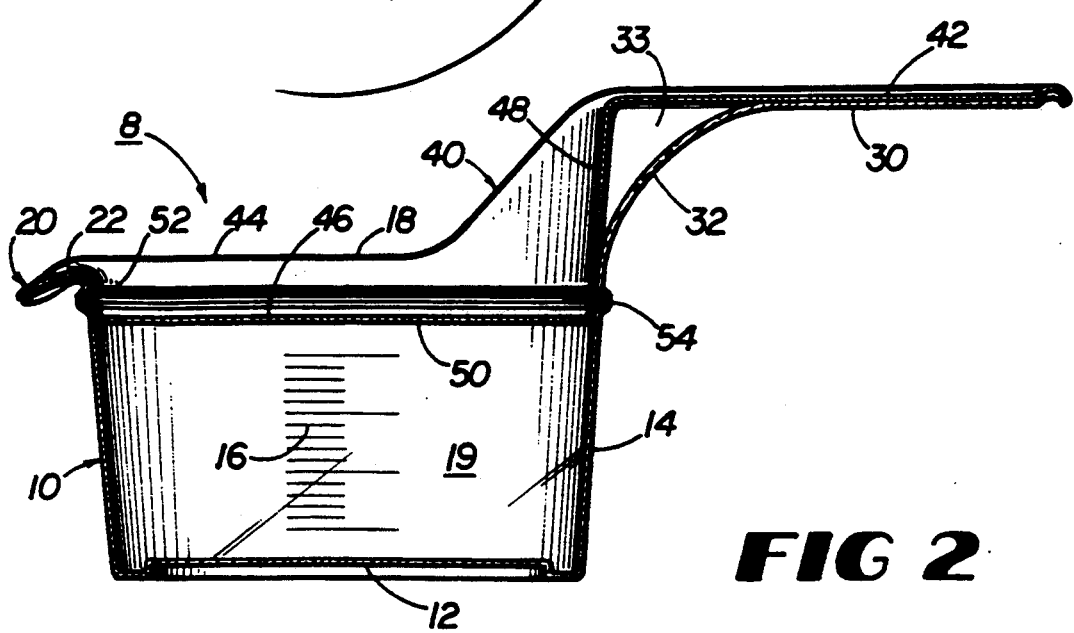
FIG. 2 is a sectional side elevation view through the center of the collection vessel and the attached cover shown in FIG. 1.

FIGS. 1 and 2 illustrate specimen container 8 of the present invention generally comprising vessel 10 and cover 40. Vessel 10 has a generally flat, oval bottom 12 and wall 14 extending substantially vertically upward therefrom. Wall 14 tilts outward at a slight angle from the bottom 12 of vessel 10, thus allowing other vessels 10 to nest for compact stacking and storage and to facilitate its manufacture. Assuming the vessel 10 is made of transparent or translucent material, such as plastic, wall 14 may have graduations 16 on one or both sides 17 and 19 that will allow an analyst to quickly and easily determine the amount of specimen collected or the appropriate amount of specimen to be transferred to another vessel for analysis.

Lip 18 runs along and outwardly from the top edge of wall 14 to rigidify vessel 10 and to prevent any of the sampled urine from flowing down the exterior of wall 14, thus further preventing spilling of the sampled urine. Lip 18 is formed into a point at the spout 20, which spout 20 contains an indentation 22 to assist pouring the collected sample into a transfer or analysis vessel.

Lip 18 extends around the edge of the vessel 10 to the handle end of vessel 10 opposite spout 20 where it forms the edge of shield 34 and of handle 30. Gusset 32 with its U-shaped channel 33 gives handle 30 sufficient rigidity to permit it to be formed of the same material with substantially the same thickness as the rest of vessel 10, thus making manufacture of the vessel simpler and correspondingly more cost effective.

FIG. 1 also shows cover 40, generally composed of the same material as vessel 10, the preferred material being plastic (either semitransparent or transparent) such as polyethylene, polypropylene, polyvinylchloride or polyethylene terephtalate or any other conventional materials known to those skilled in the art. Cover 40 includes a top panel 46, a handle 42 and a cover shield 48 that connects the panel 46 and handle 42. A rim 44 encircles the panel 46, where a placard or label (not shown) containing identifying information on the specimen may be placed. Rim 44 extends vertically upward from panel 46 so that any such label can frictionally engage rim 44 and be kept in area 46. Of course, an adhesive may also be applied to area 46 to maintain a label. Additionally, by resting on lip 18 of the vessel, rim 44 prevents cover 40 from slipping into vessel 10, and thus establishes a more reliable foundation on which filled or empty specimen containers 8 may rest.

Optional cover handle 42, which facilitates easy removal or placement of the cover, is attached to cover 40 by cover shield 48. Together, cover shield 48, panel area 46 and rim 44 of cover 40 provide a firm base to allow many covers to be stacked solidly through frictional engagement and thereby stored together. Furthermore, the underside of cover 40 is also close in size to the open portion of vessel 10 so that when placed together cover 40 tightly engages the top of vessel 10 as annular ridge 52 locks into mating recess 54. As cover 40 is lowered onto the opening of vessel 10, annular ridge 52 slightly spreads wall 14 until annular ridge 52 engages mating recess 54, permitting wall 14 to spring back to its original position and thereby forcing cover 40 into a tighter fit with vessel 10. Thus, cover 40 provides a substantially liquid tight seal for the contents of vessel 10.

FIG. 2 illustrates vessel 10 with interlocked cover 40 fully engaged. The unitary container 8 thereby created provides a sealed container for easy transport. Moreover, with labelled cover 40 attached to filled vessel 10, the now unitary container 8 is easily stacked and stored, as bottom 12 of vessel 10 will solidly engage the substantially flat panel 46, rim 44 and cover shield 48 of cover 40 of other unitary filled collection containers 8. Additionally, stacked columns of filled containers 8 can be oriented so administering personnel can immediately determine by graduations 16 the amount of specimen remaining.

The foregoing is provided for purposes of illustrating, explaining and describing one embodiment of the present invention. Modifications and adaptations to these embodiments will be apparent to those of ordinary skill in the art and may be made without departing from the scope or spirit of the invention and the following claims.

I claim:

1. A container for collecting a urine specimen comprising:
   a. a collection vessel having a substantially flat bottom defining a perimeter about which is joined a substantially vertically extending side wall to define an interior of the vessel and an upper edge that includes a recess therein and a generally horizontal and planar vessel opening, wherein the bottom width is proportionally less than its length;
   b. a shield, connecting to the upper edge of the vessel, extending substantially vertically upward above the generally horizontal plane of the vessel opening;
   c. a handle, connecting to the shield, for lifting and manipulating the vessel and including a gusset to strengthen the connection of the handle to the shield; and
   d. a cover, dimensioned to provide a substantially liquid tight seal for a urine specimen held in the interior of the collection vessel comprising:
      i) a panel dimensioned substantially to match the vessel opening, wherein the panel is capable of supporting a second urine specimen container;
      ii) an annular ridge, surrounding the panel, that interlocks with the recess; and
      iii) a rim that is capable of preventing the second urine specimen container from sliding off the panel.

2. The container of claim 1 wherein the cover further comprises means for facilitating removal from or attachment to the matching recess on the vessel.

3. The container of claim 1 further comprising means on the vessel wall to facilitate determination of the amount of liquid within the vessel.

4. The container of claim 1 wherein the vessel and cover are formed of plastic.

5. The container of claim 1 wherein the vessel and cover are formed of a clear vinyl.

6. The container of claim 1 further comprising a spout formed in the vessel to facilitate pouring liquid out of the vessel.

7. An apparatus for collecting urine specimens from female humans comprising:
 a. a generally elliptically shaped bottom whose width is less than its length;
 b. a wall, joined to the bottom, extending substantially vertically upward from the bottom to define an opening and an interior;
 c. a shield extending substantially vertically upward from the wall;
 d. a handle connected to the shield and provided with a gusset for reinforcement; and
 e. a cover suitably dimensioned to engage in a close fit with the opening of the vessel and define a generally horizontal, planar surface on which another substantially identical apparatus can be positioned, the cover comprising:
  (i) a panel dimensioned substantially to match the vessel opening;
  (ii) a ridge surrounding the panel that is received in a matching recess on the wall;
  (iii) a rim, extending for a short distance above the plane of the panel, capable of preventing the substantially identical apparatus positioned on the cover from sliding off of the cover.

8. The urine specimen collector of claim 7 wherein the cover has a second handle.

9. A urine specimen collector for easily collecting urine specimens from male or female humans and that can be easily sealed to prevent contamination or spilling of urine specimens, the collector comprising:
 a. a racetrack shaped bottom having a width less than its length and a perimeter defining a first arc joined by a first length and a second length to a second arc;
 b. a generally vertically extending wall surrounding the perimeter of the bottom and defining an interior and an opening with a top edge, which is encircled at least partially by a recess located within the interior;
 c. a first shield, located above the first arc, connecting with the recess and extending substantially vertically upward;
 d. a handle connected via a gusset to the shield; and
 e. a cover comprising:
  (i) a panel dimensioned to fit within the interior so that a ridge surrounding at least a portion of the panel interlocks with the recess to cover the opening and provide a substantially liquid proof seal preventing the urine specimen within the interior from being contaminated or leaking out;
  (ii) a second shield, extending above the ridge, dimensioned to match approximately and fit over the first shield; and
  (iii) a rim, extending above the ridge, for cooperating with the panel and shield, wherein the rim is capable of holding a second urine specimen collector on top of the cover.

* * * * *